United States Patent
Hasegawa et al.

(10) Patent No.: US 6,218,184 B1
(45) Date of Patent: Apr. 17, 2001

(54) MEDIA FOR THE TISSUE CULTURE OF PLANTS AND METHOD OF CULTURE WITH THE SAME

(75) Inventors: Osamu Hasegawa; Fumihiko Tadokoro, both of Tokyo; Nobumitsu Takahashi, Kanagawa, all of (JP)

(73) Assignees: Nisshinbo Industries Inc.; Mitsubishi Chemical Corporation, both of Tokyo (JP)

( * ) Notice: Subject to any disclaimer, the term of this patent is extended or adjusted under 35 U.S.C. 154(b) by 0 days.

(21) Appl. No.: 09/011,066

(22) PCT Filed: Jun. 18, 1997

(86) PCT No.: PCT/JP97/02088

§ 371 Date: May 28, 1998

§ 102(e) Date: May 28, 1998

(87) PCT Pub. No.: WO97/48271

PCT Pub. Date: Dec. 24, 1997

(30) Foreign Application Priority Data

Jun. 19, 1996 (JP) ................................. 8/158323
Jun. 19, 1996 (JP) ................................. 8/158325

(51) Int. Cl.$^7$ ............................................ C05G 3/00
(52) U.S. Cl. ................ 435/431; 435/410; 435/420; 47/58.1; 504/101
(58) Field of Search .................. 435/431, 420, 435/410; 47/58.1; 504/101

(56) References Cited

U.S. PATENT DOCUMENTS 4,164,405 * 8/1979 Pinckard .
5,288,775 * 2/1994 Bischoff et al. .

* cited by examiner

*Primary Examiner*—Leon B. Lankford, Jr.
(74) *Attorney, Agent, or Firm*—Arent Fox Kintner Plotkin & Kahn, PLLC (57) ABSTRACT

This invention relates to a culture medium used to efficiently propagate and acclimatize tissue cultured plantlets and thereafter obtain mature plantlets, a method to produce said medium, and a tissue culture method using said medium. The plant tissue culture medium is a novel plant tissue culture medium comprised in the main of vermiculite with an average particle diameter between 0.1–10 mm and cellulose fibers of an average fiber length between 0.01–5 mm. The culture method uses said culture medium in a light-transmissible container equipped at least in part with a porous gas permeable film, preferably having an air permeability between 1–50 sec/100 ml as measured in accordance with JIS standard P8117. The solid culture medium formed from a specific type of vermiculite and cellulose fibers enables the culturing process as a whole to be performed easily and efficiently. Root development and plant growth are good, and healthy plants can be produced in a single culturing without the need for an acclimatization stage. Plantlets can also be transplanted directly without damaging the roots. Moreover, when this medium is used in combination with a light-transmissible container equipped with a gas permeable film, the aforementioned efficacy is noticeably improved.

16 Claims, 2 Drawing Sheets

MEDIA FOR THE TISSUE CULTURE OF PLANTS AND METHOD OF CULTURE WITH THE SAME

FIELD OF INVENTION

This invention relates to a new plant tissue culture medium which can be used successively from propagation to acclimatization to the formation of the mature plantlet, and to a method for production of said medium. The invention further relates to a culture method in which this medium is used in a light-transmissible container which is at least partially equipped with a porous gas permeable film.

PRIOR ART

Cell culture and meristem culture of highier plants is a multistage process, starting from a primary culture and successive sub-cultures to form multiple axillary shoots or plantlets by such methods as "enhanced axillary branching", "protocorm-like body formation", or "shoot primordium formation", followed by the culturing of mature plantlets. Culturing of mature plantlets comprises the growth of shoots from "protocorm-like bodies", "shoot primordium" or the like, followed by differentiation of adventitious roots. In this stage, the culture medium (support material) is a critical factor in the growth and development of the root structure of the plant.

Agar is the most commonly used medium for this type of plant tissue culture. However, an agar medium cannot be aerated, this root induction is poor. Root development is better with an agar medium specifically formulated for such purpose, but the adventitious roots formed therein cannot function effectively, and when the plantlets thereof are transplanted directly into soil, the exposed foliage soon withers.

In one method in use to resolve this problem, after removal from the agar medium the plantlets are first acclimatized in perlite, vermiculite, or similar media for a period before transplanting them into soil either outdoors or in greenhouses. However, this acclimatization normally requires an extended period of one to three months, during which rooting is poor causing the plantlets to wither or die, or the plantlets remain vitrificated and cannot develop into normal plants. The method has many disadvantages in tens of time and labor and yield.

Alternatively, rockwool, or perlite and vermiculite have been used in place of agar. However, rockwool itself does not decompose when the plantlets are transplanted directly into the soil, and the root structure can be damaged upon attempting to remove it, thereby reducing the rooting ratio. Also, root growth is retarded because rockwool as a culture substrate is too hard. On the other hand, the granular structure of perlite and vermiculite make it difficult for the plants to be affixed to the medium, and this poor contact results in uneven growth rates among the plants. In addition, perlite and vermiculite are difficult to work with when planting since the granules easily stick to the tips of the forceps.

Moreover, glass, polycarbonate, or other non-porous containers are generally used in the aforementioned culture methods, but because of the poor gas permeability of these materials, the plantlets are spindly with poor root structure and cannot be transferred outdoors directly. As a result, the culture process had to be divided into two separate stages, a propagation and root induction stage, and an acclimatization stage.

These conventional plant tissue culture methods as described present many problems in acquiring mature plantlets. Root development is poor, as is primary growth, and the yield is reduced because of the poor rooting ratio. As well, the necessity of dividing the culture process into the aforementioned two stages increases both the time and labor. This invention was developed in order to resolve these problematic points.

That is, an objective of this invention was to provide a culture medium which would improve the efficiency of propagating and acclimatizing tissue cultured plants, and a method of producing said medium.

Another objective of this invention was related to a novel culture method using this culture medium.

This invention is characterized by a novel plant tissue culture medium comprised in part of vermiculite with an average particle diameter between 0.1–10 mm and cellulose fibers of an average fiber length between 0.01–5 mm; in addition, it provides a culture method in which said culture medium is used in a light-transmissible container equipped at least in part with a porous gas permeable film, preferably having an air permeability between 1–50 sec/100 ml as measured in accordance with JIS standard P8117.

The use of this culture medium formed from a specific type of vermiculite and cellulose fibers enables the culturing process as a whole to be performed easily and efficiently. Root development and plant growth are good, and healthy plants can be produced in a single culturing without the need for an acclimatization stage. Plantlets can also be transplanted directly without damaging the roots. The inventors also observed that when this medium is used in combination with a light-transmissible container equipped with a gas permeable film, the aforementioned efficacy is noticeably improved, and this invention was therein completed.

DISCLOSURE OF INVENTION

This invention provides a composite culture medium formed from vermiculite and cellulose fibers. There is no specific restriction on the type of vermiculite, but a baked vermiculite with an average particle diameter between 0.1–10 mm, preferably between 1–5 mm, is best. Pretreated vermiculite of various types can be used. Pretreatment processes include heating, cooling, refining, expansion, pulverization, pelletization, impregnation, coating, or other chemical or physical processing.

The cellulose fibers should have an average fiber length between 0.01–5 mm, preferably between 0.02–4 mm. There is no specific restriction on the type of cellulose, and cotton lint, cotton linter, softwood cellulose, hardwood cellulose, bast fiber cellulose, hemp cellulose, regenerated cellulose, bacteria-derived cellulose, or the like, or any mixture thereof can be used. As well, pretreated cellulose of various types can be used. Pretreatment processes include heating, cooling, refining, conversion to amorphous cellulose, swelling, depolymerization, chemical derivatization, crosslinking, conversion of cellulose crystalline type, regeneration from dissolved cellulose, pulverization, pelletization, impregnation, coating, or other chemical or physical processing.

The admixture ratio of vermiculite to cellulose fiber will vary with the method of molding, but a ratio between 50:50–95:5 parts by weight is preferable, more preferably in a 65:35–90:10 ratio. Cellulose ratio above or below these values are not desirable. At a ratio of less than 5% by weight, intertwining of the vermiculite and cellulose fibers is poor making the admixture difficult to mold. Conversely, if the cellulose content exceeds 50% by weight, the resultant molded product is too hard for embedding the plantlets.

The vermiculite and cellulose fibers can be molded, for example, by either of two methods, wet molding or dry compression molding. In wet molding, the vermiculite and cellulose fibers are admixed in a liquid, preferably water, and the slurry so formed is poured into a mold. The liquid is then removed and the mold is dried. In dry compression molding, an admixture of dry components is compressed.

For wet molding, the cellulose fibers should preferably have an average fiber length between 0.1–4 mm, more preferably from 0.5–3 mm. The vermiculite should preferably have an average particle diameter between 0.1–10 mm, more preferably from 0.5–5 mm. If the cellulose fibers are too short, the mold becomes too hard when dried, and is still too hard upon the addition of a nutrient liquid medium, making it difficult to embed the plantlets. Conversely, if the cellulose fibers are too long, the vermiculite and cellulose fibers cannot entwine, making it difficult to form an uniform admixture and molded product. In either case, the final product is not desirable as a culture medium.

Similarly, extremes in vermiculite particle size are not desirable. If the particles are too fine, the nutrient liquid medium cannot be effectively retained by the substrate; also, the resultant mold is too hard making it difficult to embed the plants. Conversely, if the particles are too large, the plantlets cannot be embedded at any arbitrary position within the medium, thus reducing its utility as a working medium.

Any method can be used to remove the liquid. For example, the slurry can be filtered naturally by gravity, or the liquid can be removed by centrifugation, suction, or squeezing. Nor is there any specific restriction on the drying method; for example, the product can be dried by a blow dryer, or in a constant temperature oven or a radiation dryer using electromagnetic waves or far infrared waves, or the product can be freeze-dried or dried in the sun. There is also no specific restriction on the liquid; for example, water or an organic solvent such as an alcohol, ketone, hydrocarbon, or halogenated hydrocarbon can be used, although water is preferable since it would have no adverse effect on the plants.

When a nutrient liquid medium or other liquid is added to a molded product so formed, the liquid is retained by the cellulose fibers and the vermiculite, and the structural interstices formed by the two materials. In so doing, the product becomes soft to yield a culture medium suitable for the embedding of plants.

For dry compression molding, the cellulose fibers should preferably have an average fiber length between 0.02–0.5 mm, more preferably between 0.1–0.4 mm, and the vermiculite should have an average particle diameter between 0.1–10 mm. If the cellulose fibers are too short, the molded product becomes too hard upon the addition of a nutrient liquid medium, making it difficult to embed the plantlets. Conversely, if the cellulose fibers are too long, the vermiculite and cellulose fibers cannot entwine, making it difficult to obtain a uniform admixture and difficult to mold. In either case, the molded product is not desirable as a culture medium.

Similarly, extremes in vermiculite particle size are not desirable. If the particles are too fine, the nutrient medium cannot be retained as effectively; also, the resultant mold will be too hard making it difficult to embed the plants. Conversely, if the particles are too large, the plantlets cannot be embedded at any arbitrary position within the medium, thus reducing its utility as a working medium.

For compression molding, the vermiculite and cellulose fibers should preferably be mixed in a ratio between 50:50–95:5 parts by weight, and more preferably in a 80:20–95:5 ratio. A compressive strength between 5–200 kg/cm$^2$ can normally be used. If the compressive strength is too low, the molded product will be too crumbly; conversely, if the compressive strength is too high, the product becomes too hard, making it difficult to embed the plants. In either case, the resultant product is not suitable as a culture medium.

Although there is no specific restriction on the temperature for compression, a temperature between 10–200° C. can nornally be used. A mold tends to become denser the higher the temperature, and the temperature for compression should be set so as to obtain the required density. There is also no specific restriction on the compression time, but generally a compression period of 5 seconds to 10 minutes will produce a mold that is of suitable strength and texture to enable the plant material to be easily embedded.

When a nutrient liquid medium or other liquid is added to a compression molded product so formed, the layered structure of the vermiculite expands, and the nutrient medium is retained by the cellulose fibers, the vermiculite, and the structural interstices formed by said materials. The product thus becomes pliable and soft to provide a suitable substrate within which to embed the plants.

A wet molding and dry molding method to produce the substrate have been described here, but regardless of the method employed, the addition of the nutrient liquid medium or other liquid to this substrate yields a suitably soft material into which the plant material can be embedded.

The density of these molded products should preferably be in a range from 0.05–2 g/cm$^3$, specifically the wet mold should be in a range from 0.05–1 g/cm$^3$, preferably 0.07–0.3 g/cm$^3$, and the dry mold should be in a range from 0.5–2 g/cm$^3$, preferably 0.5–1.5 g/cm$^3$. If the density is higher than these recommended values, the product so formed is too hard; and is still too hard even upon the addition of the nutrient liquid medium or other liquid, making it difficult to embed the plants. Root development is also poor. If the density is less than the recommended values, the product does not retain its shape making it difficult to work with, and again is unsuitable as a culture medium.

The vermiculite and cellulose fiber admixture of this invention can be mixed with other ingredients as long as said components do not hinder the efficacy of the product as a culture medium. Other ingredients include organic substances, organic salts, organic acids, organic bases, organic polymeric substances, inorganic substances, inorganic salts, inorganic acids, inorganic bases, high molecular weight inorganic substances, or any admixtures thereof. Examples include rockwool, perlite, peat moss, wood chips, sawdust, leaf compost, chitin, chitosan, agar, and gellan gum. In addition, activated carbon or other adsorbents can be added to prevent browning of the plant tissues, as well as bactericides and bacteriostats to reduce contamination.

The substrate so produced is admixed with a nutrient liquid medium, then sterilized in an autoclave or other sterilizing instrument before it is used as the culture medium for the propagules. In cell culture and meristem culture of higher plants, a propagule refers to the multiple shoot cluster or plantlet formed in a primary culture and successive sub-cultures by such methods as "enhanced axillary branching", "protocorm-like body formation", "adventitious shoot formation", or other organiogenic pathway.

There are no restrictions as to the type of plant that can be cultured by the method of this invention; it is applicable, for example, to Cattleya, Phalaenopsis, Dendrobium, Cymbidium, Papliopedilum, Vanda, Ascocenda, Epidendrum, Miltonia, Oncidium, Odontoglossum, Epiphronitis, Calanthe, Nephrolepis, Diffenbachia, fringed orchs, Canarium, Syngonium, Streptocarpus, Clematis, Geranium, Poinsettia, Rhododendron, Gloxinia, Alstroemeria, Hemerocallis, Freesia, Iris, carnation, baby's breath, Statis, Chrysanthemum, Transvaal daisy, Primula, Saintpaulia, Cyclamen, Lily, Gladiolus, Dalhlia, Roseaceae, Bouvardia, Azalea, Gentianaceae, Narcissus, amaryllis, hyacinth, begonia, Aster savatieri, Miltonia, Asplenium, Benjamin, Spathiphyllum, Pothos, Alocasia, Monstera, Philodendron, Syndapsis, Caladium, Ananas, Neoregalia, Dracaena, tree fern, maidenhair fern, Asplenium nidus, various ferns, Anthurium, lawn grass, strawberry, garlic, Japanese horseradish (wasabi), cucumber, tomato, eggplant, Irish potato, sweet potato, taro, yam, Chinese yam, carrot, melon, arum, butterburr, asparagus, plants of the Cruciferae family, rice, wheat, cotton, banana, pineapple, oil palm, apple, pear, persimmon, grape, peach, plum, citrus fruits, tea, raspberry, blueberry, almond, cherry, Ligusticum officinale, Pinellia ternata, Rhododendron pentaphyllum, Atractylodes japonica, belladonna, Aconitum chinense, hashiridokoro, ipecac, Japanese green gentian, rhubarb, cherry tree, paper mulberry, weeping birch, eucalyptus, rubber, paulownia, aspen, poplar, sandalwood, teak, elm, white birch, mulberry, oak (Quercus acutissima), Hiba arborvitae, cedar (cryptomeria), cypress, spruce, fir, pine, yew, sequoia, lauan, Dipterocarpaceae, Gomphrena, mahogany, and other herbs, flowering plants, trees, and other plant life.

For orchids, the medium of this invention has the advantage that it limits the growth of excessive protocorm-like bodies, eliminates the intertwining of roots, and enables roots to be disentangled without breaking them when separating plantlets. For tree species, this method is advantageous in that the seedlings can be grown in a sugarless medium, and the seedling and its substrate can be planted directly in the soil, and thereafter rooting is good. For vegetables and flowering plants, healthy plantlets with hairly roots can be cultured, and in the case of medicinal plants, the content of the medicinal component can be increased.

There is no particular restriction on the nutrient liquid medium, and a variety of media such as the normal Murashige and Skoog (MS) medium, White's medium, Vicin and Went medium, Hyponex medium, or Woody Plant medium can be used. Moreover, the nutrient liquid medium can be modified as required; for example, it can be diluted as necessary as a function of the type of plant, phosphoric acid, chelated iron, and a variety of other ingredients can be added, the sugar concentration can be changed, banana juice can be added, a variety of plant growth hormones can be added, and antibacterials and bacteriostats can be added.

The amount of nutrient liquid medium to be used will vary as a function of the type of plant and cannot be defined exactly, but a volume between 20–65 ml per 10 g of culture medium is appropriate. Too much solution will reduce the air layer to create excessive humidity, and root development will be poor causing the plant to become vitrificated. On the other hand, too little solution is unsuitable as the plant will be unable to absorb enough nutrients for growth.

Figure 1:
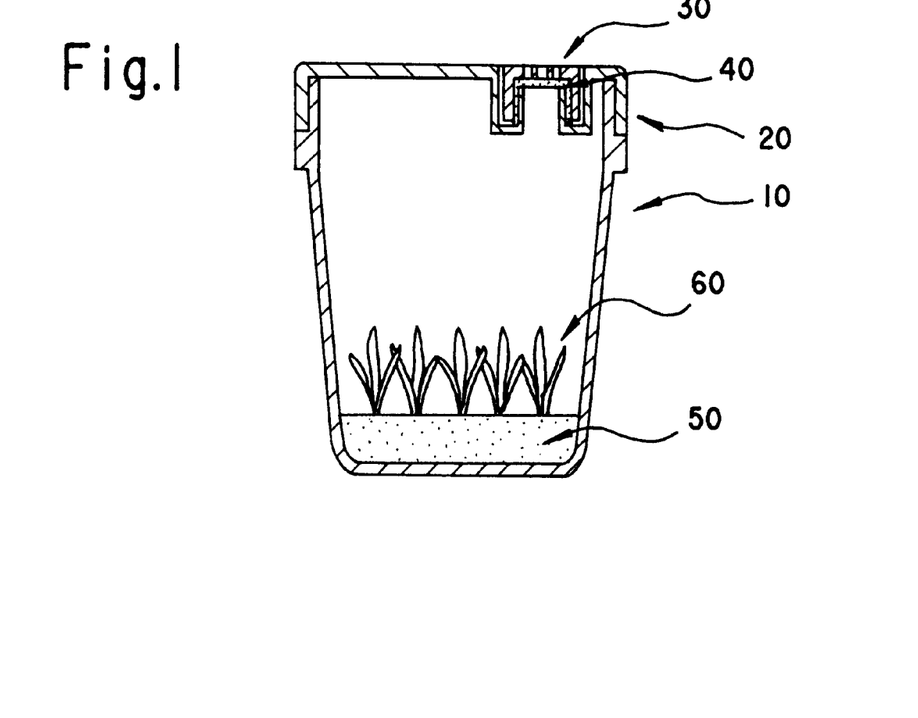
FIG. 1 is a vertical cross section diagram of the assembled components of this invention.
Figure 2:
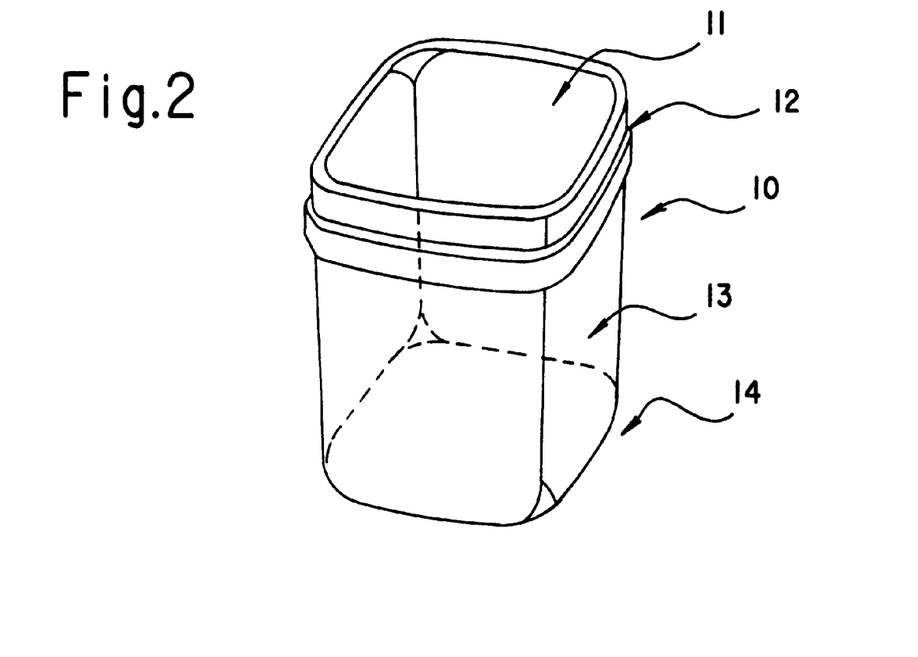
FIG. 2 is a perspective drawing of the culture container.
Figure 3:
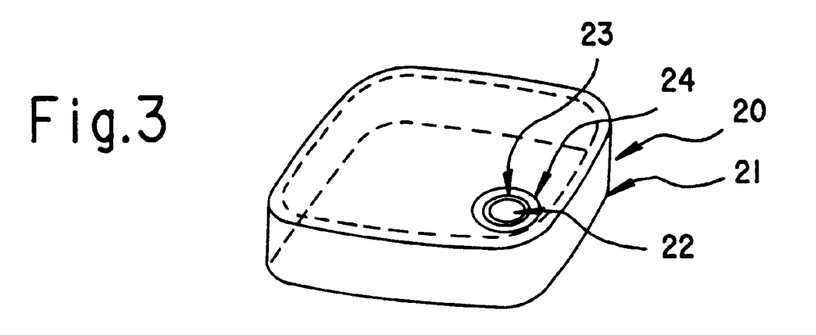
FIG. 3 is a perspective drawing of the container lid.
Figure 4:
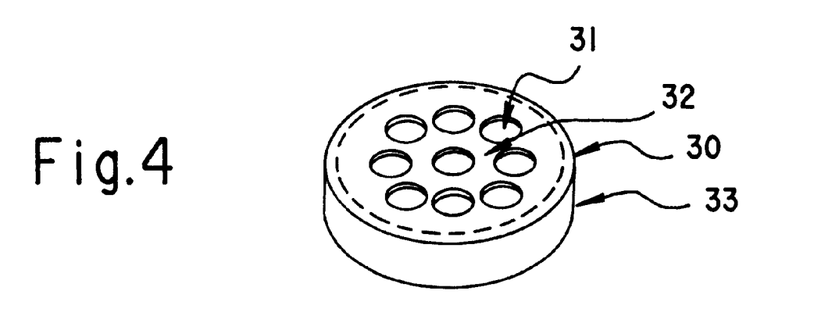
FIG. 4 is a perspective drawing of the cap.
Figure 5:
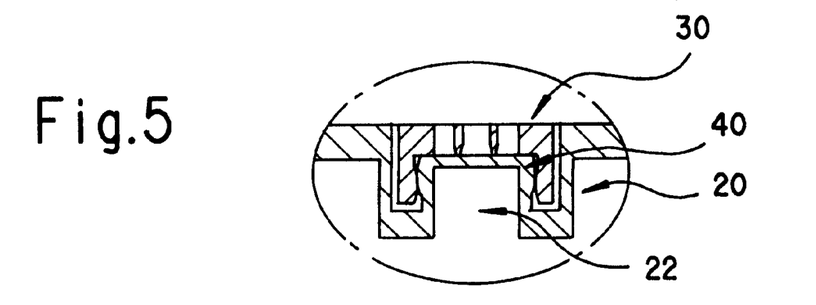
FIG. 5 is an expanded cross section diagram of the air hole segment of the lid assembly.

Although there is no particular restriction on the type of container for the culture process, the method of this invention is particularly effective if the culture vessel is a light-transmissible container equipped at least in part with a porous gas permeable film. An example of a suitable container is shown in FIGS. 1–5. Nor is there any particular restriction on the shape of the container, which in general is comprised of a vessel plus a lid. As well, there is no restriction on the composition of the container which can be made from glass, polystyrene, polyester, polyvinyl chloride, polycarbonate, polyethylene, polypropylene, or any combination product thereof; however, a polycarbonate material of good durability, heat-resistance, and light-transmission is preferable.

The size of the container is not restricted either, but should preferably be of a size that can be easily handled. It is preferable that an air hole to be bored in the container or the lid, and covered tightly with a porous gas permeable film. The film can be applied in any manner as long as it securely attached; for example, it can be gilled on with a suitable adhesive, or a cap can be laid over the film; the latter is preferable since it will enable the film to be easily removed and replaced. The area of the air hole is not restricted, but should preferably be from 0.2–4 $cm^2$ for ease of use.

The porous film should have an air permeability (as measured by JIS-P8117) between 1–50 sec/100 ml, preferably from 1–10 sec/100 ml and more preferably from 1–5 sec/100 ml. If the permeability is too low, growth and root development will be relatively poor because of low gas exchange rate, but if the permeability is too high, excessive water evaporation will cause the medium to dry out. Air flow could be increased by using a larger film of low air permeability, but that would decrease the amount of light into the container, which would have an adverse effect on the growth of the plants. Also, the film could be more easily ruptured, and other problems in terms of strength preclude this combination. For these reasons, a film of the aforementioned degree of gas permeability is most preferable in terms of practical usage.

Moreover, the gas permeable film should preferably have an average pore diameter between 0.1–10 $\mu$m, and more preferably between 0.2–1 $\mu$m. An average pore diameter greater than 10 $\mu$m is not recommended because of the possibility of contamination with various bacteria. Also, a film thickness in a range from 50–500 $\mu$m is preferable for ease-of-handling. As to the material itself, any durable material which can withstand the sterilization process can be used; for example, a polystyrene, polyester, polyamide, polypropylene, nylon, cellulose, fluorinated polymers, poly-4-methyl-1-pentene, or similar polymer can be used. A composite material of any of the aforementioned materials blended with glass fibers or the like can also be used.

In using the culture medium (support material) of this invention, in general, a nutrient liquid medium of weaker concentration than that used for an agar medium is better suited for plant growth. This is because the medium of this invention enables the nutrient liquid medium to be used more effectively than does an agar medium.

Moreover, the ingredients of the nutrient medium can be added to the vermiculite and cellulose fiber admixture before molding, thereby eliminating the time and labor of the step to add the nutrient medium.

The use of the culture medium (support material) of this invention enables good root growth, which is an extremely favorable state for the plants. As a result, the use of this culture medium will allow the acclimatization process to be eliminated, improve the yield of the plantlets, and enable direct transplantation of the plantlets into the soil thereby reducing both time and labor. Moreover, once the plantlets are transplanted, the culture medium decomposes into the soil, and as such is more environmentally friendly than rockwool.

In addition, when the culture medium of this invention is used in combination with the aforementioned culture container, the water vapor inside the container can adequately permeate through the film to prevent excessive humidity. As well, there is good exchange with gases from the external atmosphere; specifically the carbon dioxide level, which is essential to healthy plant growth, is not reduced to minute levels, and the aforementioned efficacy of the system is improved even more.

SIMPLIFIED EXPLANATION OF DIAGRAMS

PREFERRED EMBODIMENTS OF THE INVENTION

This invention is next explained in detail with the following examples; however, this invention is not restricted to these examples as long as the parameters are within the stated boundaries.

The workability of the culture medium is shown by the following symbols:

A1: Addition of nutrient liquid medium makes the culture medium soft and plantlets can be easily embedded.
A2: Medium is soft and embedding of plantlets is easy.
B: Medium is hard and embedding of plantlets is difficult even after the addition of nutrient medium.
C: Medium does not retain its shape when dried, and crumbles even with the addition of nutrient medium.
D: Cellulose fibers do not evenly entwine with the vermiculite, and the medium does not retain its shape.
E: Vermiculite particles are too large, restricting the sites for embedding of the plants.
F: Medium crumbles upon the addition of nutrient medium
G: Medium is hard and embedding of plantlets is difficult.

Evaluation of root development of the plant is shown by the following five degrees:

+++ Large root development (Very good)
++ Normal root development (Good)
+ Small root development (Poor)
± Very small root development (Very poor)
− Virtually no root development (Poorest)

Judgments as to workability of the medium, and root development, plantlet quality, and post-transplant growth as listed in the tables are all relative evaluations as observed from the experiments.

The air permeability of the porous film was measured using a Model B Galay denso meter (manufactured by Toyo Seiki Seisakusho) in accordance with JIS Method P8117.

Working Example 1 is an example of the production of the plant tissue culture medium by wet molding. One part by weight of LBKP wood pulp with an average fiber length of 1.2 mm was dispersed in 50 parts by weight of water, then 5 parts by weight of baked vermiculite (product of China) of an average particle size of 2 mm was admixed. The slurry so produced was poured onto a 355 $\mu$m mesh screen, and the solids were leveled as the water was gravity filtered to obtain a cake. After most of the water was removed, the cake was dried at 90° C., then cut into 50 mm×50 mm×20 mm cubes. The density of the product so formed after drying was 0.13 g/cm$^3$.

Working Example 2 is an example of the production of the plant tissue culture medium by dry compression molding. Nine parts by weight of dried baked vermiculite (product of China) of an average particle diameter of 2 mm was mixed with one part by weight of powdered cellulose fibers of an average fiber length of 300 $\mu$m. A sufficient quantity of this admixture was spread into a metal mold to yield a mass per unit area of 0.7 g/cm$^2$, then pressed at a compressive strength of 50 kg/cm$^2$ for one minute at room temperature. The molded product so formed was cut into 50 mm×50 mm squares. The density of the product so produced was 1 g/cm$^3$.

In Working Examples 3–12 inclusive, culture medium products were formed by the same method as used in Example 1 and Example 2, but with the particle diameter of the vermiculite and the fiber length of the cellulose being changed in each case as shown in Table 1.

Similarly, in Comparative Examples 1–12 inclusive, the culture medium products were formed by the same method as used in Example 1 and Example 2, but with the particle diameter of the vermiculite and the fiber length of the cellulose being changed in each case as shown in Table 1. In Comparative Example 13 and Comparative Example 14, the culture medium of this invention was replaced with a 0.8% agar formulation and rockwool respectively.

In Working Example 13, each culture medium produced in Working Examples 1–12 inclusive and Comparative Examples 1–14 inclusive was placed into an individual gas impermeable polycarbonate container (6 cm L×6 cm W×10 cm H), then 45 ml of a nutrient medium (prepared by adding 400 mg/l of ammonium dihydrogen phosphate ($NH_4H_2PO_4$), 33 mg/l of FeEDTA, and 3% by weight of saccharose to standard MS medium) was added to each sample. The containers were then autoclaved, after which an approximately 1 cm long, sterilized single node segment excised from a sweet potato cultured plantlet was embedded in the culture medium. Each container was then sealed and the explant was cultured at 25° C. for one month.

The workability of each culture medium in terms of the ease in embedding the explant was judged at that time, and plantlet growth in terms of weight, height, state of root development and plantlet quality were examined after culturing for one month. The plantlets were then transplanted into pots filled with vermiculite, and their growth observed over a two-week period. Results are shown in Table 1.

The culture media of the 12 Working Examples were found to be of satisfactory workability with the explants being easily embedded; moreover, plantlets cultured in these media were healthy with satisfactory root development. Good growth was also observed after transplantation.
[Insert Table 1]

In Working Example 14, the culture medium of Example 1 and Example 2 was used, and 45 ml of a nutrient liquid medium prepared by supplementing a standard MS medium with 3% saccharose was added to each container. Otherwise, the parameters were the same as for Example 13. Each container was then autoclaved, after which an approximately 3 cm long end nodal segment of a sterilized cultured carnation plantlet was embedded in the culture medium. The explant was then cultured at 20° C. for one month.

Plantlet growth in terms of weight, height, state of root development and plantlet quality were examined after culturing the explant for one month. The plantlets were then transplanted into pots filled with vermiculite, and their growth observed over a two-week period. Results are shown in Table 2.

Comparative Example 15 and Comparative Example 16 were the same carnation growth tests of Working Example 14 except that the culture medium of this invention was replaced by a 0.8% agar and rockwool respectively. Results are shown in Table 2.

The culture medium of Working Example 1 and of Working Example 2 was found to be of good workability with the explants being easily embedded; moreover, plantlets cultured in this medium were firm with good root development. Good growth was also observed after transplantation.
[Insert Table 2]

TABLE 1

| | CULTURE MEDIA | | | | | SWEET POTATO EXPERIMENTS | | | | | |
| | | | | | | | | | | After | |
| | Culture Media Components | | | | | Growth | | | | Transplantation | |
| | Vermiculite | Cellulose | | | | State After 1 Month of Culturing | | | | Rooting | |
| | Av. Particle Diam. (mm) | Av. Fiber Length (mm) | Other | Type | Workability | Weight (g) | Height (cm) | Root** | Plantlet Quality | Ratio (%) | Growth |
|---|---|---|---|---|---|---|---|---|---|---|---|
| Working Ex. 1 | 2.0 | 1.2 | — | Wet | A1 | 0.65 | 2.7 | +++ | Good | 80 | Good |
| Working Ex. 2 | 2.0 | 0.3 | — | Dry | A1 | 0.55 | 2.5 | +++ | Good | 70 | Good |
| Working Ex. 3 | 0.7 | 0.05 | — | Dry | A1 | 0.51 | 2.5 | +++ | Good | 70 | Good |
| Working Ex. 4 | 0.7 | 0.3 | — | Wet | A1 | 0.54 | 2.6 | +++ | Good | 75 | Good |
| Working Ex. 5 | 0.7 | 1.2 | — | Wet | A1 | 0.57 | 2.6 | +++ | Good | 75 | Good |
| Working Ex. 6 | 0.7 | 4 | — | Dry | A1 | 0.55 | 2.5 | +++ | Good | 70 | Good |
| Working Ex. 7 | 2.0 | 0.05 | — | Wet | A1 | 0.60 | 2.7 | +++ | Good | 75 | Good |
| Working Ex. 8 | 2.0 | 4.0 | — | Wet | A1 | 0.62 | 2.6 | +++ | Good | 80 | Good |
| Working Ex. 9 | 7.0 | 0.05 | — | Dry | A1 | 0.50 | 2.3 | +++ | Good | 70 | Good |
| Working Ex. 10 | 7.0 | 0.3 | — | Dry | A1 | 0.52 | 2.4 | +++ | Good | 70 | Good |
| Working Ex. 11 | 7.0 | 1.2 | — | Wet | A1 | 0.53 | 2.4 | +++ | Good | 75 | Good |
| Working Ex. 12 | 7.0 | 4.0 | — | Wet | A1 | 0.51 | 2.3 | +++ | Good | 70 | Good |
| Comparative Ex. 1 | — | 1.2 | — | Wet | B | 0.15 | 1.2 | ± | Poor | 0 | No growth |
| Comparative Ex. 2 | 2.0 | — | — | Wet | C | 0.45 | 2.2 | + | Poor (Variable) | 50 | Slightly retarded |
| Comparative Ex. 3 | 2.0 | 0.009 | — | Wet | B | 0.14 | 1.2 | ± | Poor | 0 | No growth |
| Comparative Ex. 4 | 2.0 | 10.0 | — | Wet | D | 0.25 | 1.8 | + | Poor | 20 | Retarded |
| Comparative Ex. 5 | 0.05 | 1.2 | — | Wet | B | 0.16 | 1.3 | ± | Poor | 0 | No growth |
| Comparative Ex. 6 | 15.0 | 1.2 | — | Wet | E | 0.34 | 2.0 | + | Poor | 30 | Retarded |
| Comparative Ex. 7 | — | 0.3 | — | Dry | B | 0.15 | 1.1 | ± | Poor | 0 | No growth |

TABLE 1-continued

| | CULTURE MEDIA | | | | SWEET POTATO EXPERIMENTS | | | | | After | |
| | | | | | | Growth | | | | Transplantation | |
| | Culture Media Components | | | | | State After 1 Month of Culturing | | | | Rooting | |
| | Vermiculite | Cellulose | | | | | | | | | |
| | Av. Particle Diam. (mm) | Av. Fiber Length (mm) | Other | Type | Work-ability | Weight (g) | Height (cm) | Root** | Plantlet Quality | Ratio (%) | Growth |
|---|---|---|---|---|---|---|---|---|---|---|---|
| Comparative Ex. 8 | 2.0 | — | — | Dry | F | 0.43 | 2.2 | + | Poor (Variable) | 50 | Slightly retarded |
| Comparative Ex. 9 | 2.0 | 0.009 | — | Dry | B | 0.19 | 1.5 | ± | Poor | 0 | No growth |
| Comparative Ex. 10 | 2.0 | 10.0 | — | Dry | D | 0.27 | 1.9 | + | Poor | 20 | Retarded |
| Comparative Ex. 11 | 0.05 | 0.3 | — | Dry | B | 0.14 | 1.2 | ± | Poor | 0 | No growth |
| Comparative Ex. 12 | 15.0 | 0.3 | — | Dry | E | 0.30 | 1.9 | + | Poor | 25 | Retarded |
| Comparative Ex. 13 | — | — | Agar | — | A2 | 0.40 | 2.7 | + | Poor (Spindly) | 25 | Retarded |
| Comparative Ex. 14 | — | — | Rockwool | — | G | 0.20 | 1.5 | ± | Poor | 40 | Slightly retarded |

Root** = Root development

TABLE 2

| | CULTURE MEDIA | | | | CARNATION EXPERIMENTS | | | | | After | |
| | | | | | | Growth State After 1 Month of Culturing | | | | Transplantation | |
| | Culture Media Components | | | | | | | | | Rooting | |
| | Vermiculite | Cellulose | | | | | | | | | |
| | Av. Particle Diam. (mm) | Av. Fiber Length (mm) | Other | Type | Work-ability | Weight (g) | Height (cm) | Root** | Plantlet Quality | Ratio (%) | Growth |
|---|---|---|---|---|---|---|---|---|---|---|---|
| Working Ex. 14 | 2.0 | 1.2 | — | Wet | A1 | 0.26 | 8.0 | +++ | Good | 50 | Good |
| | 2.0 | 0.3 | — | Dry | A1 | 0.25 | 7.8 | +++ | Good | 50 | Good |
| Comparative Ex. 14 | — | — | Agar | — | A2 | 0.13 | 7.5 | + | Poor (Spindly) | 20 | Retarded |
| Comparative Ex. 16 | — | — | Rockwool | — | G | 0.10 | 7.0 | ± | Poor (Vitrification) | 10 | Retarded |

Root** = Root development

Working Example 15 followed the experiment of Working Example 13 in which the culture medium of Working Example 1 was used. The container was injection molded and of a type as shown in FIGS. 1–5 (bottom face: 70 mm×70 mm, opening: 90 mm×90 mm, height: 120 mm, thickness: 1.5 mm). The lid, with a 10 mm diameter air hole, had a tight fit with the container. A polypropylene cap was used to secure the porous film and its bottom face was perfectly flush with the film with no gap. An air hole was bored in the cap so as to align perfectly with the air hole in the lid. The following types of porous film were then set in place to form the culture vessel.

| (a) | E01008E | Manufacturer: | Nihon Pall Ltd. |
| | | Thickness: | 200 μm |
| | | Average pore diameter: | 0.3 μm |
| | | Air permeability: | 2 sec/100 ml |
| | | Composition: | Glass fiber mesh/ cellulose filter |
| (b) | Hydrolon | Manufacturer: | Nihon Pall Ltd. |
| | | Thickness: | 160 μm |
| | | Average pore diameter: | 1.2 μm |
| | | Air permeability: | 7 sec/100 ml |
| | | Composition: | Nylon |
| (c) | Biodyne A | Manufacturer: | Nihon Pall Ltd. |
| | | Thickness: | 150 μm |
| | | Average pore diameter: | 0.5 μm |
| | | Air permeability: | 30 sec/100 ml |
| | | Composition: | Nylon |

Results of sweet potato growth experiments using the culture vessels so produced are shown in Table 3.

Comparative Example 17 was the same as the sweet potato growth experiment of Working Example 15 except that the aforementioned films (a)–(c) were replaced by the following films (d)–(f) respectively.

| | | |
|---|---|---|
| (d) HDCIIj006 | Manufactured by Nihon Pall Ltd. | |
| | Thickness: | 200 μm |
| | Average pore diameter: | 0.6 μm |
| | Air permeability: | 70 sec/100 ml |
| | Composition: | Glass fiber mesh/cellulose filter |
| (e) Polypropylene film | Thickness: | 50 μm |
| | Air permeability: | Infinite sec/100 ml |
| (f) Non-woven cotton cloth Oikos PL2050 | Manufacturer: | Nisshinbo Industries, Inc. |
| | Mass per unit area: | 50 g/m$^2$ |
| | Air permeability: | 0.1 sec/100 ml |

Results are shown in Table 3.

Comparative Example 18 was the same as the sweet potato growth experiment of Working Example 15 except that film (a) was used and a 0.8% agar was used as the culture medium. In addition, the sweet potato growth experiment of Comparative Example 17 was conducted using film (e) and a 0.8% agar as the culture medium. Results are shown in Table 3.

Comparative Example 19 was the same as the sweet potato growth experiment of Working Example 15 except that film (a) and the culture medium of Comparative Example 5 was used. Results are shown in Table 3.

Plantlets cultured using a container having a porous film with an air permeability between 1–50 sec/ml and the culture median of Working Example 1 were healthy with good root development. There was no drying or other problems, and good growth was also observed after transplantation of the plantlets.

[Insert Table 3]

Working Example 16 was a carnation growth experiment in which the parameters were the same as for Working Example 15 except that the culture medium of Working Example 2 and the nutrient liquid medium of Working Example 14 was used. Results are shown in Table 4.

Working Example 17 was a carnation growth experiment in which the parameters were the same as for Working Example 16 except that no sucrose was added to the standard MS medium. Results are shown in Table 4.

Comparative Example 20 was a carnation growth experiment in which the parameters were the same as for Working Example 16 except that the film of Comparative Example 17 was used. Results are shown in Table 4.

Comparative Example 21 was a carnation growth experiment in which the parameters were the same as for Working Example 17 except that the film of Comparative Example 17 was used. Results are shown in Table 4.

Comparative Example 22 was a carnation growth experiment in which the parameters were the same as for Working Example 16 except that film (a) of Working Example 15 and a 0.8% agar was used. In addition, the carnation growth experiment of Comparative Example 20 was conducted using the polypropylene film (e) of Comparative Example 17 and a 0.8% agar. Results are shown in Table 4.

Comparative Example 23 was a carnation growth experiment in which the parameters were the same as for Working Example 17 except that film (a) of Working Example 15 and a 0.8% agar was used. In addition, the carnation growth experiment of Comparative Example 21 was conducted using the polypropylene film (e) of Comparative Example 17 and a 0.8% agar. Results are shown in Table 4.

Comparative Example 24 was a carnation growth experiment in which the parameters were the same as for Working Example 16 except that film (a) of Working Example 15 and a rockwool was used. In addition, the carnation growth experiment of Comparative Example 20 was conducted using the polypropylene film (e) of Comparative Example 17 and a rockwool. Results are shown in Table 4.

Comparative Example 25 was a carnation growth experiment in which the parameters were the same as for Working Example 17 except that film (a) of Working Example 15 and a rockwool was used. In addition, the carnation growth experiment of Comparative Example 21 was conducted using the polypropylene film (e) of Comparative Example 17 and a rockwool. Results are shown in Table 4.

Plantlets cultured using a container having a porous film with an air permeability between 1–50 sec/ml and the culture medium of Working Example 2 were healthy with good root development using nutrient liquid medium systems with or without sugar. There was no drying or other

TABLE 3

| | | | | SWEET POTATO EXPERIMENTS | | | | | |
|---|---|---|---|---|---|---|---|---|---|
| | | | | | Growth State After 1 Month of Culturing | | | | After Transplantation |
| | | Air Permeability | | | | | | Rooting | |
| | Culture Medium Composition | of Porous Film (sec/ml) | Workability of Culture Medium | Weight (g) | Height (cm) | Root Development | Plantlet Quality | Ratio (%) | Growth |
| Working Ex. 15 | Same as Working Example 1 | 2 | A1 | 0.90 | 3.0 | +++ | Very good | 100 | Good |
| | | 7 | A1 | 0.90 | 3.0 | +++ | Very good | 100 | Good |
| | | 30 | A1 | 0.80 | 2.8 | +++ | Good | 100 | Good |
| Comparative Ex. 17 | | 70 | A1 | 0.67 | 2.7 | ++ | Below average | 80 | Slightly retarded |
| | | ∞ | A1 | 0.65 | 2.7 | ++ | Below average | 80 | Slightly retarded |
| | | 0.1 | A1 | 0.30 | 2.0 | + | Poor (Medium dried; growth uneven) | 30 | Very retarded |
| Comparative Ex. 18 | Agar | 2 | A2 | 0.51 | 2.6 | + | Poor (Agar dried up, roots damaged) | 40 | Retarded |
| | | ∞ | A2 | 0.40 | 2.7 | + | Poor (Spindly) | 25 | Very retarded |
| Comparative Ex. 19 | Same as Comparative Example 5 | 2 | B | 0.18 | 1.2 | ± | Poor | 0 | No growth | problems, and good growth was also observed after transplantation of the plantlets.
[Insert Table 4]

Example 18 except that half-strength MS medium without any sugar supplement was used. Results are shown in Table 5.

TABLE 4

| | | Air Permeability of Porous Film (sec/ml) | Workability of Culture Medium | Nutrient Medium | CARNATION EXPERIMENTS | | | | | |
|---|---|---|---|---|---|---|---|---|---|---|
| | Culture Medium Composition | | | | Growth State After 1 Month of Culturing | | | | After Transplantation | |
| | | | | | Weight (g) | Height (cm) | Root Development | Plantlet Quality | Rooting Ratio (%) | Growth |
| Working Ex. 16 | Same as Working Example 2 | 2 | A1 | With sugar | 0.46 | 9.0 | +++ | Very good | 100 | Good |
| Working Ex. 17 | | | | No sugar | 0.40 | 7.5 | +++ | Very good | 100 | Good |
| Working Ex. 16 | | 7 | | With sugar | 0.34 | 8.5 | +++ | Very good | 100 | Good |
| Working Ex. 17 | | | | No sugar | 0.30 | 7.5 | +++ | Very good | 100 | Good |
| Working Ex. 16 | | 30 | | With sugar | 0.34 | 8.5 | +++ | Good | 100 | Good |
| Working Ex. 17 | | | | No sugar | 0.28 | 7.0 | +++ | Good | 100 | Good |
| Comparative Ex. 20 | | 70 | | With sugar | 0.27 | 8.0 | ++ | Below average | 70 | Slightly retarded |
| Comparative Ex. 21 | | | | No sugar | 0.12 | 5.3 | + | Below average | 70 | Slightly retarded |
| Comparative Ex. 20 | | ∞ | | With sugar | 0.25 | 7.8 | ++ | Below average | 50 | Slightly retarded |
| Comparative Ex. 21 | | | | No sugar | 0.10 | 5.0 | + | Mediocre | 50 | Slightly retarded |
| Comparative Ex. 20 | | 0.1 | | With sugar | 0.10 | 3.0 | ± | Poor (Medium dried, growth uneven) | 0 | No growth |
| Comparative Ex. 21 | | | | No sugar | 0 | 0 | − | No growth | 0 | No growth |
| Comparative Ex. 22 | Agar | 2 | A2 | With sugar | 0.22 | 4.7 | + | Poor (Medium dried, roots damaged) | 30 | Retarded |
| Comparative Ex. 23 | | | | No sugar | 0 | 0 | − | No growth | 0 | No growth |
| Comparative Ex. 22 | | ∞ | | With sugar | 0.13 | 7.5 | + | Very poor (Spindly) | 20 | Retarded |
| Comparative Ex. 23 | | | | No sugar | 0 | 0 | − | No growth | 0 | No growth |
| Comparative Ex. 24 | Rockwool | 2 | G | With sugar | 0.25 | 5.6 | + | Very poor (Roots broke when separating shoots) | 20 | Retarded |
| Comparative Ex. 25 | | | | No sugar | 0 | 0 | − | No growth | 0 | No growth |
| Comparative Ex. 24 | | ∞ | | With sugar | 0.10 | 7.0 | ± | Very poor (Vetrification) | 10 | Very retarded |
| Comparative Ex. 25 | | | | No sugar | 0 | 0 | — | No growth | 0 | No growth |

Working Example 18 was a Japanese horseradish (hereinafter "wasabi") growth experiment in which the parameters were the same as for Working Example 16 except that the culture medium of Working Example 1 and a half-strength MS medium supplemented with 3% saccharose was used. An approximately 2 cm long single node segment excised from a sterilized cultured wasabi plantlet was embedded in the medium and cultured for six weeks at 17° C. The plantlets were then transplanted directly without washing off the culture medium into pots filled with vermiculite, and their growth was monitored for seven weeks. Results are shown in Table 5.

Working Example 19 was a wasabi growth experiment in which the parameters were the same as for Working Comparative Example 26 was a wasabi growth experiment in which the parameters were the same as for Working Example 18 except that the film of Comparative Example 17 was used. Results are shown in Table 5.

Comparative Example 27 was a wasabi growth experiment in which the parameters were the same as for Working Example 19 except that the film of Comparative Example 17 was used. Results are shown in Table 5.

Comparative Example 28 was a wasabi growth experiment in which the parameters were the same as for Working Example 18 except that film (a) of Working Example 15 and a 0.2% Gelrite was used. In addition, the wasabi growth experiment of Comparative Example 26 was conducted using the polypropylene film (e) of Comparative Example 17 and a 0.2% Gelrite. Results are shown in Table 5.

Comparative Example 29 was a wasabi growth experiment in which the parameters were the same as for Working Example 19 except that film (a) of Working Example 15 and a 0.2% Gelrite was used. In addition, the wasabi growth experiment of Comparative Example 27 was conducted using the polypropylene film (e) of Comparative Example 17 and 0.2% Gelrite. Results are shown in Table 5.

Plantlets cultured using a container having a porous film with an air permeability between 1–50 sec/ml and the culture medium of Working Example 1 were healthy with good root development using nutrient liquid medium systems with or without sugar. There was no drying out or other problems, and good growth was also observed after transplantation of the plantlets.
[Insert Table 5]

Example 20 except that no sugar was added to the Woody Plant medium (formulated as half-strength Woody Plant medium, 0.7 mg/l IBA, and 0.06 mg/l NAA). Results are shown in Table 6.

Comparative Example 30 was an oak growth experiment in which the parameters were the same as for Working Example 20 except that the polypropylene film (e) of Comparative Example 17 was used. Results are shown in Table 6.

Comparative Example 31 was an oak growth experiment in which the parameters were the same as for Working Example 21 except that the polypropylene film (e) of Comparative Example 17 was used. Results are shown in Table 6.

Comparative Example 32 was an oak growth experiment in which the parameters were the same as for Working

TABLE 5

| | Culture Medium Composition | Air Permeability of Porous Film (sec/ml) | Workability of Culture Medium | Nutrient Medium | WASABI EXPERIMENTS | | | | | |
|---|---|---|---|---|---|---|---|---|---|---|
| | | | | | Growth State After 6 Weeks of Culturing | | | | After Transplantation | |
| | | | | | Weight (g) | Height (cm) | Root Development | Plantlet Quality | Rooting Ratio (%) | Growth |
| Working Ex. 18 | Same as Working Example 1 | 2 | A1 | With sugar | 0.54 | 6.0 | +++ | Very good | 100 | Good |
| Working Ex. 19 | | | | No sugar | 0.50 | 5.9 | +++ | Very good | 90 | Good |
| Working Ex. 18 | | 7 | | With sugar | 0.50 | 6.0 | +++ | Very good | 100 | Good |
| Working Ex. 19 | | | | No sugar | 0.45 | 5.8 | +++ | Very good | 90 | Good |
| Working Ex. 18 | | 30 | | With sugar | 0.50 | 5.5 | +++ | Very good | 100 | Good |
| Working Ex. 19 | | | | No sugar | 0.45 | 5.5 | +++ | Very good | 85 | Good |
| Comparative Ex. 26 | | 70 | | With sugar | 0.40 | 5.0 | ++ | Good | 80 | Good |
| Comparative Ex. 27 | | | | No sugar | 0.30 | 4.0 | ++ | Good | 60 | Good |
| Comparative Ex. 26 | | ∞ | | With sugar | 0.35 | 5.0 | ++ | Below average | 70 | Slightly retarded |
| Cumparative Ex. 27 | | | | No sugar | 0.25 | 3.0 | + | Below average | 50 | Slightly retarded |
| Comparative Ex. 26 | | 0.1 | | With sugar | 0.10 | 2.0 | ± | Very mediocre | 0 | No growth |
| Comparative Ex. 27 | | | | No sugar | 0 | 0 | − | No growth | 0 | No growth |
| Comparative Ex. 28 | Gelrite | 2 | A2 | With sugar | 0.20 | 3.3 | ± | Mediocre | 30 | Retarded |
| Comparative Ex. 29 | | | | No sugar | 0 | 0 | − | No growth | 0 | No growth |
| Comparative Ex. 28 | | ∞ | | With sugar | 0.22 | 3.7 | + | Mediocre | 40 | Retarded |
| Comparative Ex. 29 | | | | No sugar | 0 | 0 | − | No growth | 0 | No growth |

Working Example 20 was an oak (Quercus acutissima) growth experiment in which the parameters were the same as for Working Example 18 except that the porous film (a) of Working Example 15 and a half-strength Woody Plant medium supplemented with 2% saccharose, 0.7 mg/l IBA (1H-indole-3-butanoic acid), and 0.06 mg/l NAA (1-naphthaleneacetic acid) was used. An approximately 1.5 cm long single node segment excised from a sterilized cultured oak plantlet was embedded into the medium and cultured for two months at 25° C. Results are shown in Table 6.

Working Example 21 was an oak growth experiment in which the parameters were the same as for Working Example 20 except that a 0.8% agar was used. Results are shown in Table 6.

Comparative Example 33 was an oak growth experiment in which the parameters were the same as for Working Example 21 except that a 0.8% agar was used. Results are shown in Table 6.

Comparative Example 34 was an oak growth experiment in which the parameters were the same as for Comparative Example 30 except that a 0.8% agar was used. Results are shown in Table 6.

Comparative Example 35 was an oak growth experiment in which the parameters were the same as for Comparative Example 31 except that a 0.8% agar was used. Results are shown in Table 6.

Plantlets cultured using a container having a porous film with an air permeability between 1–50 sec/ml and the culture medium of Working Example 1 were healthy with good root development using nutrient liquid medium systems with or without sugar. There was no drying out or other problems, and good growth was also observed after transplantation of the plantlets.
[Insert Table 6]

Plantlets cultured using a container having a porous film with an air permeability between 1–50 sec/ml and the culture medium of Working Example 1 were healthy with good root development. There was no drying out or other problems, and good growth was also observed after transplantation of the plantlets.

The roots and dried culture medium stuck to the bottom of the container when using the agar, but the roots did not

TABLE 6

|  | Culture Medium Composition | Air Permeability of Porous Film (sec/ml) | Workability of Culture Medium | Nutrient Medium | OAK EXPERIMENTS Growth State After 2 Months of Culturing | | |
|---|---|---|---|---|---|---|---|
|  |  |  |  |  | Height (cm) | Root Development | Plantlet Quality |
| Working Ex. 20 | Same as Working Example 1 | 2 | A1 | With sugar | 2.8 | +++ | Very good |
| Working Ex. 21 |  |  |  | No sugar | 2.4 | ++ | Very good |
| Comparative Ex. 30 |  | ∞ |  | With sugar | 2.3 | ++ | Good |
| Comparative Ex. 31 |  |  |  | No sugar | 2.0 | + | Good |
| Comparative Ex. 32 | Agar | 2 | A2 | With sugar | 2.3 | + | Fairly poor |
| Comparative Ex. 33 |  |  |  | No sugar | 1.6 (Withered) | ± | No growth |
| Comparative Ex. 34 |  | ∞ |  | With sugar | 2.2 | + | Fairly poor |
| Comparative Ex. 35 |  |  |  | No sugar | 2.5 (Withered) | ± | No growth |

Working Example 22 was a Cymbidium growth experiment in which the parameters were the same as for Working Example 20 except that Hyponex medium supplemented with 2% saccharose was used as the nutrient medium. Two Cymbidium protocorm-like bodies were embedded in the culture medium and cultured with 14 hours light-10 hours dark sequence for three months at 25° C., and growth was monitored thereafter as to plant height, root development, and plantlet quality. Results are shown in Table 7.

Comparative Example 36 was a Cymbidium growth experiment in which the parameters were the same as for Working Example 22 except that the polypropylene film (e) of Comparative Example 17 was used. Results are shown in Table 7.

stick to the container with the culture medium of Working Example 1. Growth of protocorm-like bodies was observed in the agar culture medium but not in the medium of Working Example 1. Moreover, cleaning agar off the roots was a time-consuming process, and the roots of individual plants were entangled. This phenomenon was not observed with the median of Working Example 1, and even long roots were easily separated without any breakage. Plant growth after transplantation was also much more satisfactory with plants cultured in the medium of Working Example 1.

[Insert Table 7]

TABLE 7

|  | Culture Medium Composition | Air Permeability of Porous Film (sec/ml) | Workability of Culture Medium | CYMBIDIUM EXPERIMENTS Growth State After 3 Months of Culturing | | |
|---|---|---|---|---|---|---|
|  |  |  |  | Height (cm) | Root Development | Plantlet Quality |
| Working Ex. 22 | Same as Example 1 | 2 | A1 | 6.6 | +++ | Very good |
| Comparative Ex. 36 |  | ∞ |  | 5.7 | ++ | Good |
| Comparative Ex. 37 | Agar | 2 | A2 | 3.7 | + | Not good[1] |
| Comparative Ex. 38 |  | ∞ |  | 4.0 | + | Fairly poor[2] |

[1]Agar was bone dry and could not be separated from the roots. Also, roots of different plants were entwined and broke when attempting to separate the plants.
[2]Protocorm-like body growth was present. Also, roots of different plants were entwined and broke when attempting to separate the plants.

Comparative Example 37 was a Cymbidium growth experiment in which the parameters were the same as for Working Example 22 except that a 0.8% agar was used. Results are shown in Table 7.

Comparative Example 38 was a Cymbidium growth experiment in which the parameters were the same as for Comparative Example 36 except that a 0.8% agar was used. Results are shown in Table 7.

Feasibility of Industrial Application

The working examples clearly show that the substrate of this invention enables explants to be embedded easily and the culturing process as a whole to be performed efficiently. Root development and plant growth is more satisfactory than with the conventional agar medium and rockwool. Rooting and yield are satisfactory, in which case healthy plants can be produced in a single culturing without the need for an acclimatization stage, and plantlets can be transplanted directly without damaging the roots. Addition of sugar can be omitted with this medium, thus simplifying the sterilization process. Contamination problems are also reduced. Moreover, when this medium is used in combination with a light-transmissible container having a gas permeable film with an air permeability between 1–50 sec/ml, the aforementioned efficacy is noticeably improved, and the method of this invention is therefore much more advantageous than conventional methods.

What is claimed is:

1. A plant tissue culture medium comprising vermiculite with an average particle diameter between 0.1–10 mm and cellulose fibers of an average fiber length between 0.01–5 mm.

2. The plant tissue culture medium as claimed in claim 1, wherein the ratio of said vermiculite to said cellulose fibers ranges from 50:50–95:5 parts by weight.

3. The plant tissue culture medium as claimed in claim 1, wherein the density of said medium ranges from 0.01–2 g/cm$^3$.

4. A method for producing a plant tissue culture medium, comprising the following steps:

dispersing vermiculite with an average particle diameter and cellulose fibers of an average fiber length in a liquid;

mixing said vermiculite and said cellulose fibers to form a mixture;

molding said mixture; and then drying the molded mixture to obtain said plant tissue culture medium;

wherein the average particle diameter of said vermiculite is between 0.1–10 mm, and the average fiber length of said cellulose fibers is between 0.01–5 mm.

5. A method for producing a plant tissue culture medium, comprising the following steps:

mixing vermiculite with an average particle diameter and cellulose fibers of an average fiber length in a dry state to form a mixture; and then compression molding said mixture at a compression strength between 5 kg/cm$^2$–200 kg/cm$^2$ to obtain said plant tissue culture medium;

wherein the average particle diameter of said vermiculite is between 0.1–10 mm, and the average fiber length of said cellulose fibers is between 0.01–5 mm.

6. A plant tissue culture medium produced by the method as claimed in claim 4.

7. A plant tissue culture medium produced by the method as claimed in claim 5.

8. A method for culturing a plant, comprising the following steps:

providing a culture vessel, wherein said culture vessel is a light-transmissible container having an air hole covered by a porous gas permeable film with an air permeability between 1–50 sec/100 ml;

putting the plant tissue culture medium of claim 1, 2, 3, 6 or 7 in said culture vessel;

optionally sterilizing said plant tissue culture medium in said culture vessel;

embedding the plant in said plant tissue culture medium; and then letting said plant grow in said plant tissue culture medium.

9. The plant tissue culture medium as claimed in claim 1, wherein the average particle diameter of said vermiculite is 1–5 mm.

10. The plant tissue culture medium as claimed in claim 1, wherein the average fiber length of said cellulose fibers is 0.2–4 mm.

11. The plant tissue culture medium as claimed in claim 2, wherein the ratio of said vermiculite to said cellulose fibers ranges from 65:35–90:10 parts by weight.

12. The method as claimed in claim 4, wherein the average particle diameter of said vermiculite is 0.5–5 mm.

13. The method as claimed in claim 4, wherein the average fiber length of said cellulose fibers is 0.1–4 mm.

14. The method as claimed in claim 13, wherein the average fiber length of said cellulose fibers is 0.5–3 mm.

15. The method as claimed in claim 5, wherein the average fiber length of said cellulose fibers is 0.02–0.5 mm.

16. The method as claimed in claim 15, wherein the average fiber length of said cellulose fibers is 0.1–0.4 mm.

* * * * *